US011352660B2

(12) United States Patent
Sternson et al.

(10) Patent No.: US 11,352,660 B2
(45) Date of Patent: Jun. 7, 2022

(54) MATERIALS AND METHODS FOR SERIAL MULTIPLEXED DETECTION OF RNA IN CELLS AND TISSUES

(71) Applicant: Howard Hughes Medical Institute, Chevy Chase, MD (US)

(72) Inventors: Scott Sternson, Chevy Chase, MD (US); Fredrick Henry, Chevy Chase, MD (US); Hui Yang, Chevy Chase, MD (US); Shengjin Xu, Chevy Chase, MD (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 429 days.

(21) Appl. No.: 15/724,693

(22) Filed: Oct. 4, 2017

(65) Prior Publication Data
US 2018/0094305 A1  Apr. 5, 2018

Related U.S. Application Data

(60) Provisional application No. 62/403,904, filed on Oct. 4, 2016.

(51) Int. Cl.
| | | |
|---|---|---|
| C12Q 1/68 | (2018.01) | |
| C12Q 1/6841 | (2018.01) | |
| C12Q 1/6876 | (2018.01) | |
| C12Q 1/682 | (2018.01) | |

(52) U.S. Cl.
CPC ......... *C12Q 1/6841* (2013.01); *C12Q 1/682* (2013.01); *C12Q 1/6876* (2013.01)

(58) Field of Classification Search
USPC ..... 435/6.1, 6.11, 91.1, 283.1, 287.1, 287.2; 436/94, 501; 536/23.1, 24.3, 24.33
See application file for complete search history.

(56) References Cited

U.S. PATENT DOCUMENTS

2013/0171621 A1   7/2013  Luo et al.

OTHER PUBLICATIONS

Lubeck et al., Single-cell in situ RNA profiling by sequential hybridization. Nature Methods, 11, 360 and 361, 2014.*
Supplementary Information of Nature Methods, 11, 360 and 361, 2014.*
Lubeck et al., Single-cell systems biology by super-resolution imaging and combinatorial labeling. Nature Methods, 9, 743-748, 2012.*
The definition of Ribonuclease H from Wikipedia, the free encyclopedia. Printed on Feb. 14, 2020.*
"In situ hybridization" from Wikipedia. Printed on Aug. 21, 2020.*
"Transport cross membranes". Printed on Aug. 21, 2020.*
Battich et al., "Image-based transcriptomics in thousands of single human cells at single-molecule resolution," Nature Methods, Nov. 2013, 10(11):1127-33, 10 pages.
Betley et al., "Neurons for hunger and thirst transmit a negative-valence teaching signal," Nature, May 2015, 521(7551):180-185, 39 pages.

(Continued)

*Primary Examiner* — Frank W Lu
(74) *Attorney, Agent, or Firm* — Fish & Richardson P.C.

(57) ABSTRACT

This disclosure describes materials and methods for effectively performing serial multiplexed FISH analysis.

9 Claims, 13 Drawing Sheets
(11 of 13 Drawing Sheet(s) Filed in Color)

(56) References Cited

OTHER PUBLICATIONS

Bloss et al., "Structured dendritic inhibition supports branch-selective integration in CA1 pyramidal cells," Neuron, Mar. 2016, 89(5):1016-1030, 16 pages.
Chen et al., "Spatially resolved, highly multiplexed RNA profiling in single cells," Science, Apr. 2015, 348(6233):aaa6090, 36 pages.
Economo et al., "A platform for brain-wide imaging and reconstruction of individual neurons," eLife, Jan. 2016, e10566, 22 pages.
Ke et al., "In situ sequencing for RNA analysis in preserved tissue and cells," Nature Methods, Sep. 2013, 10(9):857-860, 6 pages.
Lee et al., "Highly multiplexed subcellular RNA sequencing in situ," Science, Mar. 2014, 343(6177):1360-1363, 12 pages.
Player et al., "Single-copy gene detection using branched DNA (bDNA) in situ hybridization," The Histochemical Society, Inc., 2001, 49(5):603-611, 9 pages.
Sofroniew et al., "A large field of view two-photon mesoscope with subcellular resolution for in vivo imaging," eLife, Jun. 2016, e14472, 20 pages.
Wang et al., "A novel in situ RNA analysis platform for formalin-fixed, paraffin-embedded tissues," J. Mol. Diag., Jan. 2012, 14(1):22-29, 8 pages.

\* cited by examiner

MATERIALS AND METHODS FOR SERIAL MULTIPLEXED DETECTION OF RNA IN CELLS AND TISSUES

CROSS REFERENCE TO RELATED APPLICATIONS

This application claims the benefit of priority under 35 U.S.C. § 119(e) to U.S. Application No. 62/403,904 filed Oct. 4, 2016.

TECHNICAL FIELD

This disclosure generally relates to materials and methods for serial multiplexed detection of nucleic acids in cells and tissues.

BACKGROUND

Ribonucleic acid (RNA) is the product of gene transcription from deoxynucleic acid (DNA) that forms the template for protein biosynthesis. In addition to their role in protein translation, it is well known that nucleic acids molecules exhibit other diverse biological functions. Thus, the expression level and molecular identity of nucleic acid species needs to be measured with a high level of spatial resolution in their tissue of origin in order to understanding the relationship between gene expression and cellular phenotype. This is particularly true in complex heterogeneous tissues such as, for example, the nervous system, where numerous cell types can be distinguished by different gene expression profiles and whose functional characteristics appear to be an essential component of the complexity of the brain.

SUMMARY

Materials and methods for effectively performing serial multiplexed FISH analysis are provided herein.

In one aspect, a method of analyzing the RNA in a cell or a tissue is provided. Such a method typically includes contacting a cell or a tissue with a first DNA probe set, wherein the first DNA probe set binds to a first set of RNAs; contacting the first probe set-bound cell or tissue with RNase H to remove the first probe set; contacting the cell or the tissue with a second probe set, wherein the second DNA probe set binds to a second set of RNAs. In some embodiments, the contacting step is by a branched DNA (bDNA) RNA-single molecule (sm) fluorescent in situ hybridization (FISH) method.

In some embodiments, such a method further includes contacting the second probe set-bound cell or tissue with RNase H to remove the second probe set; and contacting the cell or the tissue with a third probe set, wherein the third DNA probe set binds to a third set of RNAs.

In some embodiments, such a method further includes contacting the third probe set-bound cell or tissue with RNase H to remove the third probe set; and contacting the cell or the tissue with a fourth probe set, wherein the fourth DNA probe set binds to a fourth set of RNAs.

In some embodiments, such a method further includes contacting the fourth probe set-bound cell or tissue with RNase H to remove the fourth probe set; and contacting the cell or the tissue with a fifth probe set, wherein the fifth DNA probe set binds to a fifth set of RNAs.

In some embodiments, such a method further includes washing the cell or the tissue after the RNase H contacting step to remove the removed probe set and the RNase H. In some embodiments, such a method further includes imaging the cell or the tissue after the probe set contacting step.

In some embodiments, the DNA probe set includes at least one DNA oligonucleotide probe. In some embodiments, the DNA probe set includes a plurality of DNA oligonucleotide probes. In some embodiments, each DNA oligonucleotide probe in the DNA probe set includes a differentially detectable label.

In one aspect, a method of analyzing the RNA in a cell or a tissue is provided. Such a method typically includes contacting a cell or a tissue with a first DNA probe set, wherein the first DNA probe set binds to a first set of RNAs; contacting the first probe set-bound cell or tissue with DNase to remove the first probe set; contacting the cell or the tissue with a second probe set, wherein the second DNA probe set binds to a second set of RNAs. In some embodiments, the contacting step is by a branched DNA (bDNA) RNA-single molecule (sm) fluorescent in situ hybridization (FISH) method. In some embodiments, such a method can further include washing the cell or the tissue after the DNase contacting step to remove the removed probe set and the DNase.

In some embodiments, such a method can further include contacting the second probe set-bound cell or tissue with DNase to remove the second probe set; and contacting the cell or the tissue with a third probe set, wherein the third DNA probe set binds to a third set of RNAs. In some embodiments, such a method can further include contacting the third probe set-bound cell or tissue with DNase to remove the third probe set; and contacting the cell or the tissue with a fourth probe set, wherein the fourth DNA probe set binds to a fourth set of RNAs. In some embodiments, such a method can further include contacting the fourth probe set-bound cell or tissue with DNase to remove the fourth probe set; and contacting the cell or the tissue with a fifth probe set, wherein the fifth DNA probe set binds to a fifth set of RNAs.

In some embodiments, such a method can further include imaging the first probe set-bound cell or tissue. In some embodiments, such a method can further include imaging the second probe set-bound cell or tissue. In some embodiments, such a method can further include aligning the second probe set-bound cell or tissue with the first probe set-bound cell or tissue.

In some embodiments, the DNA probe set includes at least one DNA oligonucleotide probe. In some embodiments, the DNA probe set includes a plurality of DNA oligonucleotide probes. In some embodiments, each DNA oligonucleotide probe in the DNA probe set includes a differentially detectable label.

In another aspect, an article of manufacture is provided. Such an article of manufacture typically includes at least one DNA probe set, wherein the at least one DNA probe set binds to a set of RNAs; and RNase H. In some embodiments, such an article of manufacture further includes reagents for hybridizing, selectively, the at least one DNA probe set to the set of RNAs.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

The patent or application file contains at least one drawing executed in color. Copies of this patent or patent application publication with color drawings will be provided by the Office upon request and payment of the necessary fee.

It was demonstrated that, after performing branched DNA/RNA smFISH, tissue treatment with RNaseH digestion of RNA-DNA hybrids followed by mild thermal stripping of the remaining branched DNA hybridization tree led to robust removal of probe-related signal that did not return after subsequent re-amplification steps. FIG. 5 shows that the smFISH signal for AgRP (left) was effectively removed after a 20 min exposure to RNaseH at 40° C. to degrade DNA/RNA complexes (middle; and step 1 in cartoon schematic above photographs). An additional step involving a 30 min incubation at 65° C. in H2O (step 2 in cartoon) served to inactivate RNase H and remove the branched DNA chain (after degradation of the mRNA/DNA complex), and re-amplification with AMP1-3 revealed low to undetectable levels of bDNA-related signal, indicating successful stripping (right).

DETAILED DESCRIPTION

A number of techniques have been developed in recent years to obtain measurements of gene expression on a single cell level. Sequencing or PCR-based methods, while highly quantitative, typically require dissociation of tissue sections into homogenous single cell suspensions for further processing, thus removing valuable information regarding the spatial arrangements of cells with unique combinations of gene expression. In contrast to such methods, image-based readouts of gene expression, including single molecule fluorescent in situ hybridization (smFISH) of RNA (sometimes referred to as RNA-smFISH), allows visualization of individual transcripts in large groups of single cells without gross disturbance of their spatial arrangement.

A widely used approach for smFISH of RNA uses a combination of oligonucleotides labeled with multiple fluorophores to "tile" the length of an mRNA species of interest. This method, sometimes referred to as o-nuc smFISH, contains no true signal amplification; only the linear combination of oligonucleotide-associated fluorophores that line the transcript of interest.

Figure 1:
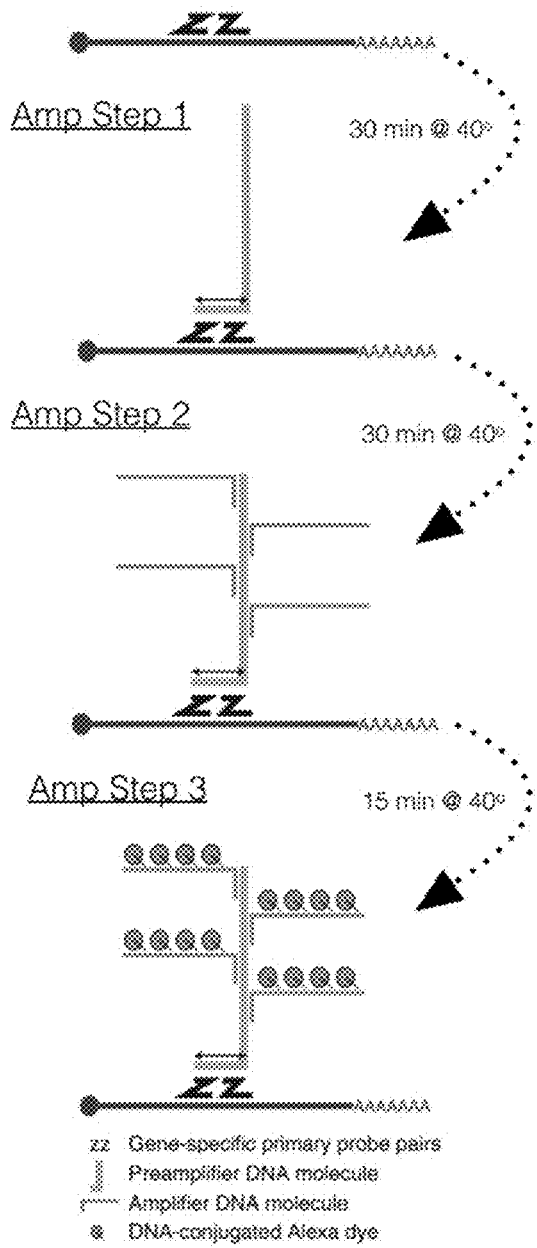
FIG. 1 is a schematic showing the branched DNA (bDNA) smFISH methods. Adapted from Battich et al., 2013, Nature Methods, 10:1127-33.

A second approach uses multiple pairs of primary DNA probes designed to hybridize to two adjacent regions, each 20-30 nucleotides in length, at several sites along the length of a transcript. These combinations of primary probes then provide hybridization sites for a second pre-amplification probe, which allows hybridization of multiple amplification probes that serve as binding regions for fluorescently conjugated DNA molecules (FIG. 1; adapted from Battich et al., 2013, Nature Methods, 10:1127-33). FIG. 1 shows signal amplification via the step-wise addition of 1) sequence-specific primary probes; 2) pre-amplification DNA molecules; 3) amplification DNA molecules; and 4) fluorophore-conjugated DNA probes. The resulting tree-like structure takes on the appearance of a DNA pillar with many branches, hence the common referral of this method as branched DNA (bDNA) RNA-smFISH. bDNA RNA-smFISH or variants thereof (e.g., MER-FISH) are suitable for use in the methods described herein. For example, Player et al., 2001, J. Histochem. Cytochem., 49 (5):603-12; Wang et al., 2012, J. Mol. Diag., 14 (1):22-9; Battich et al., 2013, Nature Methods, 10:1127-33; Ke et al., 2013, Nat. Methods, 10 (9):857-60; Lee et al., 2014, Science, 343 (6177):1360-3; Chen et al., 2015, Science, 348 (6233):aaa6090; and US 2013/0171621, all of which are incorporated herein by reference in their entirety, describe various multiplex assays.

The additional amplification sites in bDNA-based methods provide a high signal-to-noise compared with other approaches. A recent side-by-side comparison indicated that bDNA-labeled mRNA spots were roughly 100 times ("100×") brighter than those tiled with fluorescently conjugated oligonucleotides (Battich, et al., 2013, Nature Methods, 10:1127-33). Current commercial application of bDNA-based methods in conjunction with smFISH allow simultaneous labeling of up to four mRNA species in a single piece of tissue via the combined use of separate oligonucleotide sequences for both the mRNA detection and the associated signal amplification systems. Current limits on the number of mRNA species able to be differentiated in this manner are constrained by the number of oligonucleotide sequences for the branched DNA detection process as well as spectral separation between the fluorophores used in the final amplification step.

The high signal-to-noise readout of bDNA-labeled mRNA provides a distinct advantage for image-based methods to assess the presence of genes having a low level of expression, as is often the case with many important mRNA products in neurons (e.g., encoding transcription factors, neuropeptide receptors, etc.). However, there is often a need to visualize the expression of multiple genes simultaneously ("multiplexing") in a piece of tissue.

Efforts to perform multiplexed smFISH are typically limited by the number of independent signals representing distinct hybridization targets that can be read out during a single imaging round. To increase multiplexing, and thus, the number of genes whose transcripts can be quantified in a given cell, techniques have been developed to permit multiple rounds of mRNA/DNA duplex hybridization. These techniques include, for example, thermal stripping of probes bound to in situ mRNA molecules, photobleaching of fluorophores present on the hybridized molecules, and treatment with the DNA digesting enzyme, DNase. It has been determined, however, that these existing methods for serial multiplexed RNA in situ hybridization are, in practice, not suitable for multiple rounds of probe hybridization and bDNA signal amplification in sensitive tissues such as brain.

Given such difficulties, recent efforts have led to the development of new methods for removing bDNA probes from previously labeled tissue, thus permitting multiple rounds of three-plex mRNA labeling in brain tissue with little to no disturbance of tissue integrity. This disclosure describes such a method and was used to achieve multiplexed labeling of more than 9 genes (e.g., more than 10 genes, more than 12 genes, more than 15 genes) in situ with high signal-to-noise using sequential rounds of bDNA-based RNA-smFISH and enzymatic stripping of the hybridized RNA transcript. This method, referred to herein as "smart" (serial multiplexing by ablation of RNA targets) FISH, allows for reliable ex vivo detection of genes expressed at low levels, preserves tissue integrity across imaging rounds, and is suitable for combined use with other labeling techniques, including immunohistochemical protein labeling.

smartFISH provides a new implementation for RNaseH, an enzyme that selectively hydrolyzes RNA that is hybridized to DNA and is widely used, for example, in cloning techniques to eliminate RNA-DNA hybrids. While RNase H has been used previously to degrade mRNA post-cDNA conversion for the purpose of in situ sequencing, RNase H has not been used to selectively and repetitively strip DNA-RNA hybrids during identification of distinct mRNA species in cells, tissues, organs, or organisms.

Another approach, referred to as multiFISH, provide an implementation for DNase (e.g., DNase I) in repeated rounds of stripping after bDNA RNA-smFISH against mRNA. This method avoids the modestly elevated temperatures (65° C.) used in the RNase H stripping method. DNase is an enzyme that catalyzes the hydrolytic cleavage of phosphodiester bonds in the backbone of the DNA. While DNase has been used previously for multiplexed FISH, it has not been applied to bDNA FISH. In addition, prior implementations of multiplexed FISH using DNase stripping have not use fully automated alignment of tissue sections after each round of FISH due to loss binding of a nuclear stain (e.g., DAPI) due to digestion of nuclear DNA by DNase during the probe stripping process. In the multiFISH method, tissue labeled with bDNA probes for RNA-FISH can be stripped with DNase (e.g., 20 Kunitz units of DNase I in 100 μl of a DNase I buffer, such as RDD buffer from Quiagen, for 4 h), which can be inactivated, for example, by washing in phosphate buffered saline (PBS). This method ensures thorough removal of the probes and permits subsequent re-probing.

Multiple rounds of FISH on the same tissue requires alignment of a reference tissue features across each round. Cells or tissue treated with RNase H retain bright nuclear staining, which allows for simple alignment of tissue sections across multiple rounds of FISH based on aligning the cellular nuclei with standard image registration programs, such as those available in the open source image analysis software FIJI. After DNase I treatment, however, DAPI stains a combination of nuclear and high frequency fibrous non-nuclear features that are stable across multiple rounds of FISH. Using these stable DAPI-binding features, non-linear registration algorithms can be used to align three-dimensional images of these tissue sections with high precision by combining three-dimensional affine transformation and non-linear deformation transformation using, for example the Advanced Normalization Tools software package. This algorithm achieves automated computational alignment of cells or tissues across multiple rounds of FISH images. For example, alignment can be performed with cellular resolution of a single tissue sample over at least four rounds of three-plex FISH (i.e., a total of twelve FISH probes).

The high signal to noise detection of mRNA molecules present at a wide range of expression profiles in the smart- FISH and multiFISH protocols described herein, coupled with the degree to which tissue integrity is preserved, will permit seamless integration into pipelines involving post-hoc analysis of tissue that has been previously involved in any number of procedures including, without limitation, in vivo Ca2+ imaging (Betley et al., 2015, Nature, 521:180-5; Sofroniew et al., 2016, Elife, 5pii:e14472); fine scale assessment of synaptic connectivity using large volume array-tomography (Bloss et al., 2016, Neuron, 89 (5):1016-30); and cell type identification via molecular profiling after high density reconstruction with improved methods for serial two-photon tomography (Economo et al., 2016, Elife, 5:e10566).

Widespread implementation of the approach described herein enables the unbiased classification of functionally relevant gene expression profiles without making complicated and unnecessary perturbations to the cell or tissue. The procedure is relatively straightforward, able to be accomplished using commercially available reagents, and cost-limited only by the number of genes one wishes to detect in a given experiment. smartFISH and multiFISH can be incorporated into a wide variety of other imaging approaches in order to couple gene expression profiles with functional and/or anatomical data sets. The possibility of assembling these types of extraordinarily rich multi-modal data sets, as well as the ability to perform such experiments in any species for which accurate information has been acquired about the molecular profiles of cells in a given region, make smartFISH and multiFISH extremely powerful methods.

While operating at a lower throughput than methods able to profile hundreds of mRNAs species in situ, the methodology described herein will be useful for those looking to assess many (e.g., 10, 20, 30 or more) transcript types in situ under a very high signal to noise regime. To the knowledge of the inventors, there have been no published reports of successful smFISH multiplexing via sequential hybridization and stripping of bDNA probes. In addition, the methods described herein have been successfully demonstrated in complex tissues while other approaches have been limited to cell culture systems.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Ineffective Stripping Via Warm Water Exposure

Figure 2:
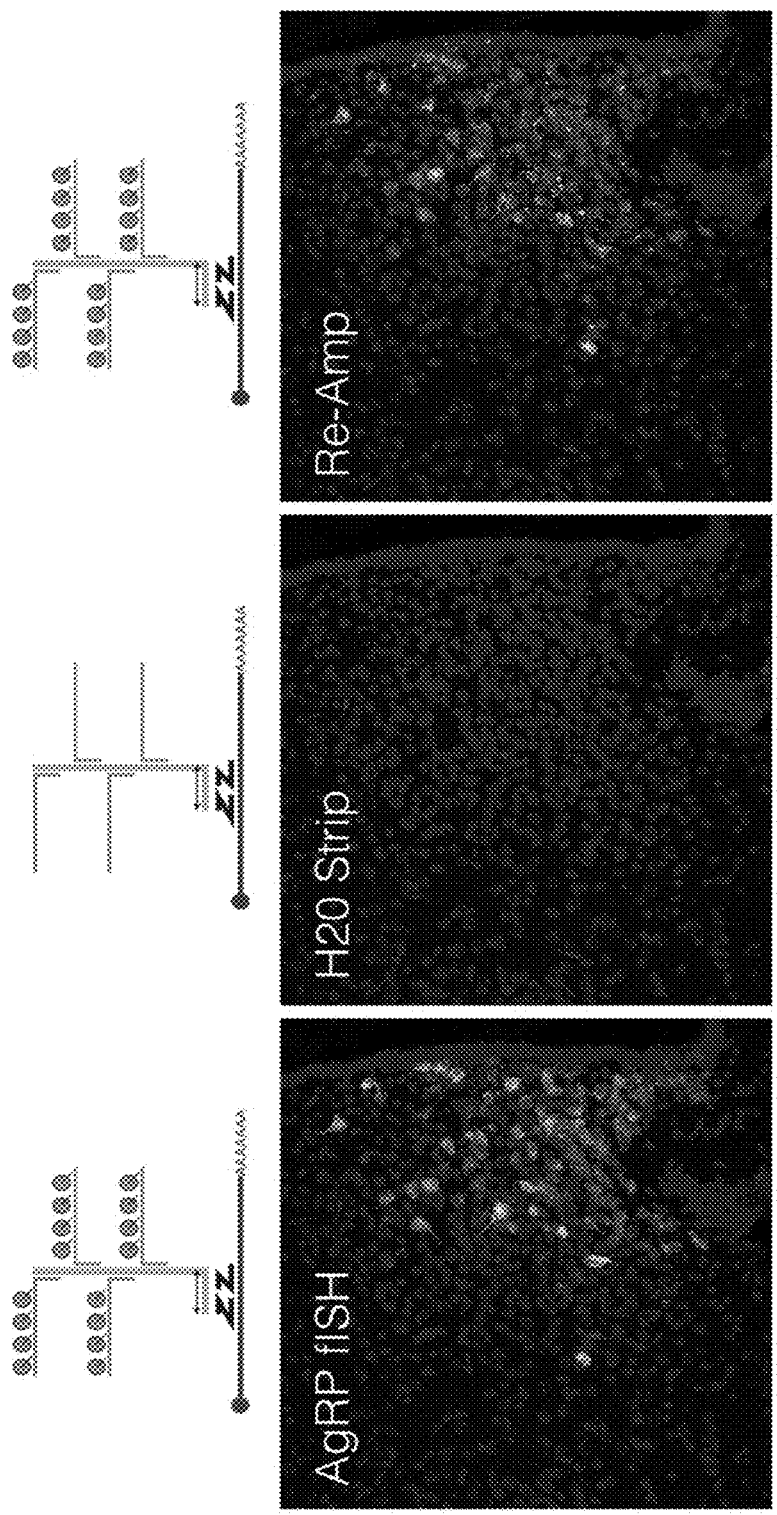
FIG. 2 are photographs that demonstrate ineffective stripping via warm water exposure. Left panel, bDNA FISH amplification and binding with AgRP (white) as well as the nuclear stain, DAPI (blue, 4'6-diamidino-2-phenylindole); Center panel, bDNA FISH following warm water stripping removes the fluorescent signal; Right panel, second bDNA FISH amplification and binding. Schematics above each image correspond to the relevant portions of the schematic shown in FIG. 1.

It was determined that, probably because of the stability of core elements of the branched DNA tree, thermal stripping, using conditions that were compatible with tissue integrity, was incomplete. FIG. 2 shows that the smFISH signal for AgRP (left) was effectively removed after 2 hrs of incubation in H2O at 37° C. (middle). However, exposing the tissue to rounds 1-3 of amplification resulted in robust detection of earlier "stripped" signal (right), indicating successful removal of the fluorophore-containing component of the branched DNA chain (AMP3 from FIG. 1) but insufficient removal of the DNA/mRNA complex itself.

Example 2—Ineffective Stripping Via Light Exposure or Photobleaching

Figure 3:
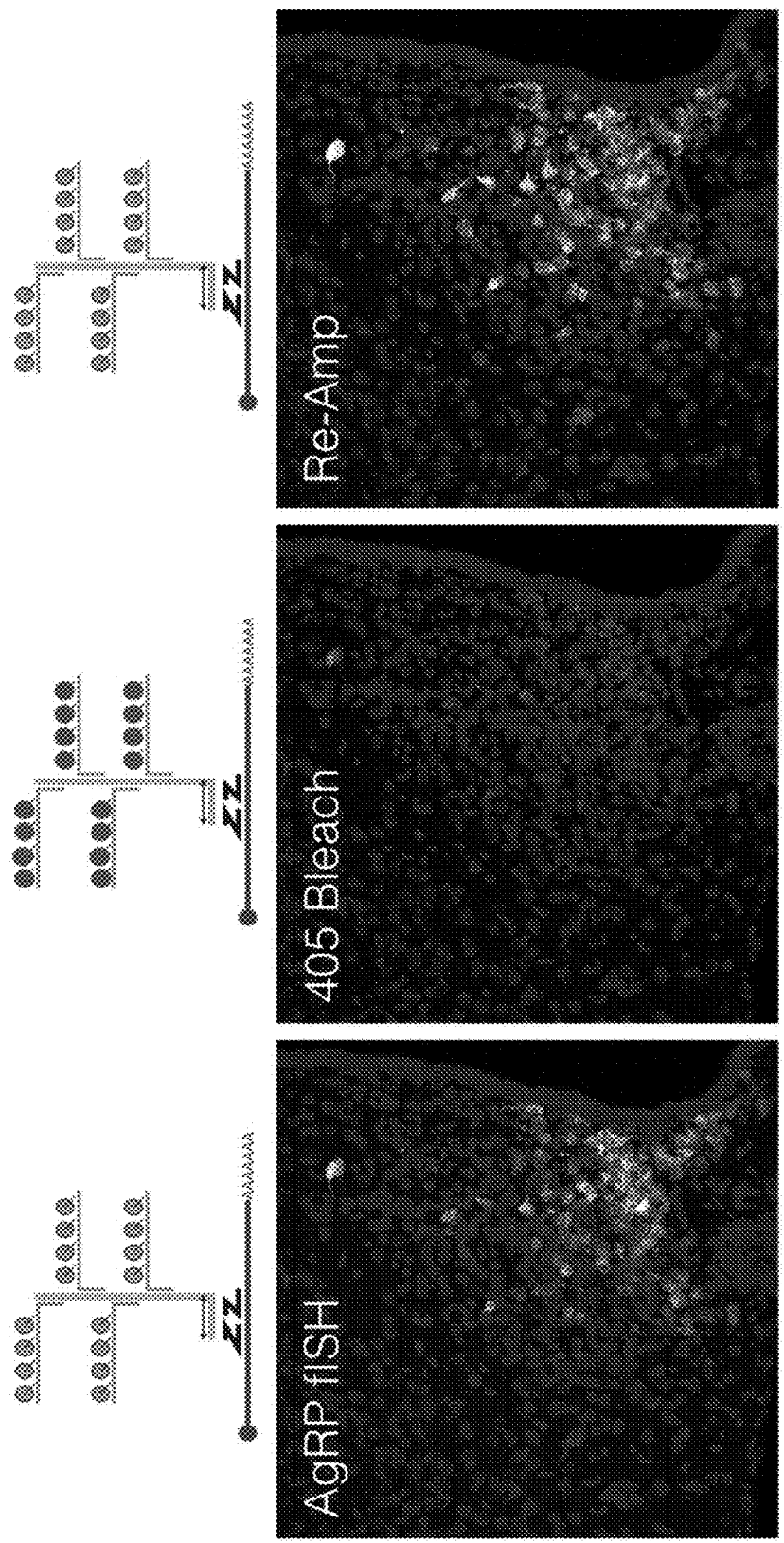
FIG. 3 are photographs that demonstrate ineffective stripping via photobleaching. Left panel, bDNA FISH amplification and binding with AgRP; Center panel, bDNA FISH following stripping by photobleaching; Right panel, second bDNA FISH amplification and binding. Schematics above each image correspond to the relevant portions of the schematic shown in FIG. 1.

It was demonstrated that photobleaching did not prevent hybridization in later rounds from detecting RNA species from earlier rounds, presumably because the oligonucleotide with the conjugated bleached fluorophore unbinds and another fluorophore-labeled oligonucleotide binds to the remaining branched DNA tree in the subsequent hybridization round (cartoon schematic above photographs). FIG. 3 shows that the smFISH signal for AgRP (left) was effectively removed after a 5 min exposure to high intensity 405 nm wavelength light (middle). However, exposing the tissue to rounds 1-3 of amplification resulted in robust detection of earlier "stripped" signal (right), indicating incomplete removal of mRNA/DNA probe complexes. Similar results were obtained after photobleaching using light at 488, 555, or 647 nm (data not shown).

Example 3—Tissue Integrity Appeared to be Compromised After Stripping By DNAse

Figure 4:
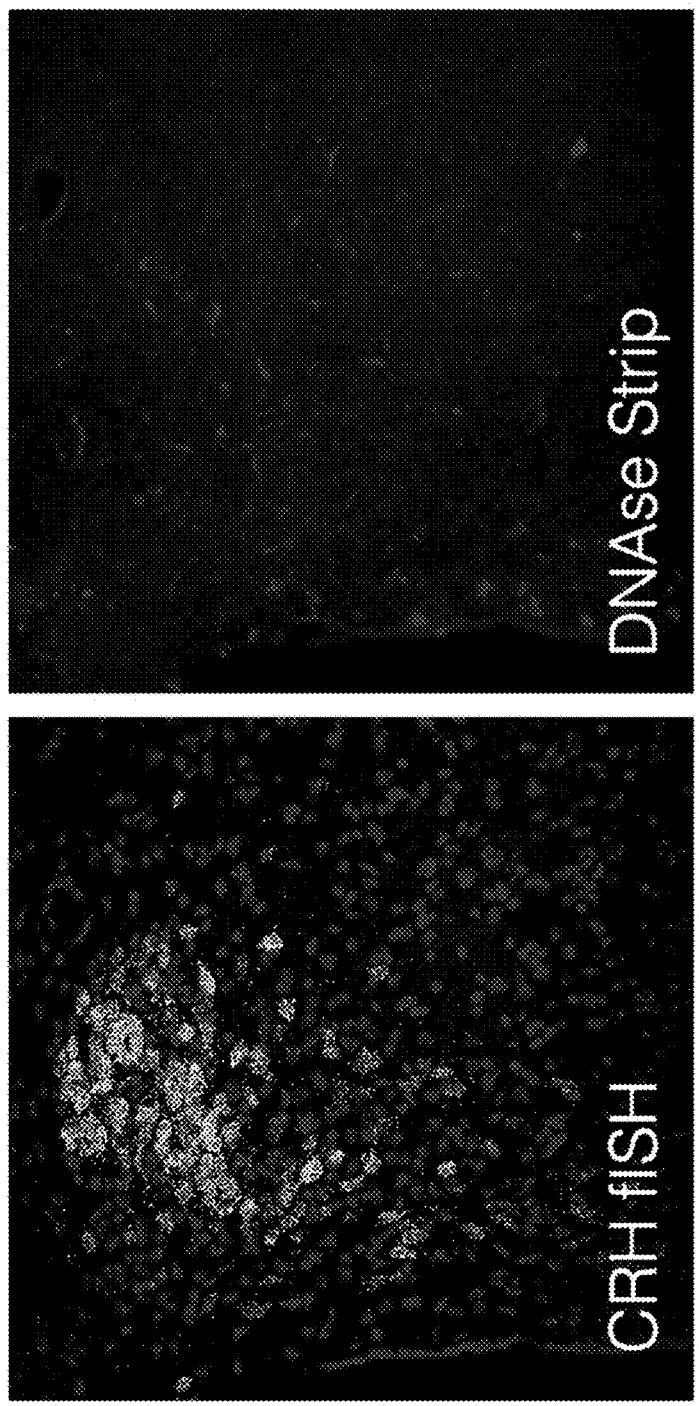
FIG. 4 are photographs showing that integrity of the DAPI nuclear stain is severely compromised after stripping by DNAse. Because nuclear stain is often used to align tissue sections across multiple rounds of FISH, this creates computational challenges after stripping with DNase. Left panel, bDNA FISH amplification and binding with CRH; Right panel, bDNA FISH following stripping with DNase.

It also was determined that, while DNase treatment effectively eliminated smFISH signal after re-amplification, it also led to a loss of tissue integrity that makes multiple hybridization events difficult. FIG. 4 shows that the smFISH signal for CRH (left, white) was effectively removed after hydrolytic cleavage of phosphodiester bonds in bDNA trees (middle). However, this enzymatic degradation process caused some amount of damage to the surrounding tissue, as evidenced by distortion of DAPI staining of cell nuclei. Because the retention of fine-grained cellularity in situ is paramount to the success of implementing a detection strategy involving multiple rounds of labeling, a different alignment protocol was required when using DNAse (see Example 9 below).

Example 4—Effective Enzymatic Removal of bDNA FISH Probes Using RNase H

Figure 5:
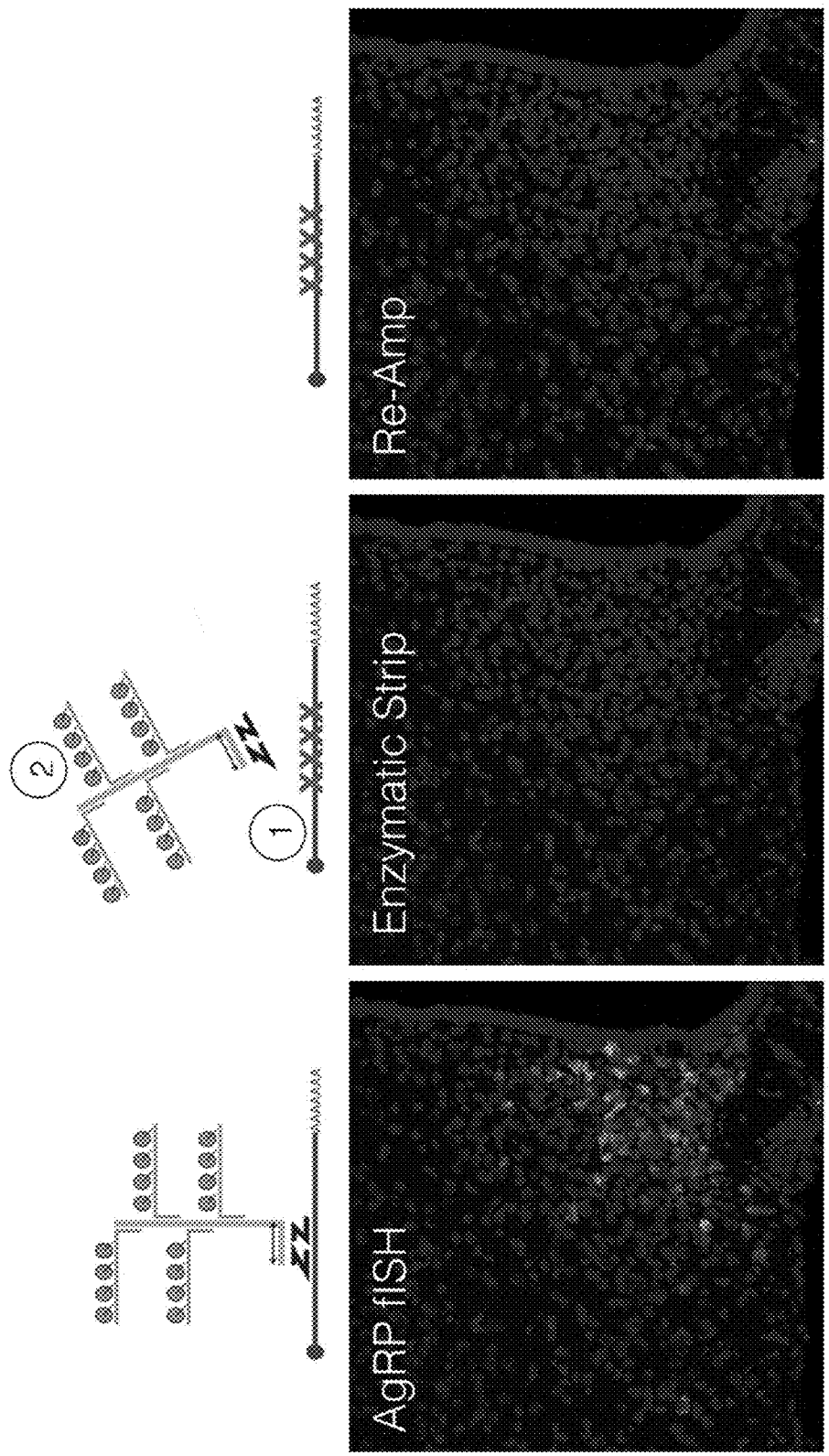
FIG. 5 are photographs showing effective removal of bDNA FISH probes using RNaseH. Left panel, bDNA FISH amplification and binding with AgRP; Center panel, bDNA FISH following enzymatic stripping with RNase H; Right panel, second bDNA FISH amplification and binding. Schematics above each image correspond to the relevant portions of the schematic shown in FIG. 1; red X's indicate that the mRNA that was previously bound to the bDNA probe is selectively digested and, thus, the entire bDNA tree is removed.

It was demonstrated that, after performing branched DNA/RNA smFISH, tissue treatment with RNaseH digestion of RNA-DNA hybrids followed by mild thermal stripping of the remaining branched DNA hybridization tree led to robust removal of probe-related signal that did not return after subsequent re-amplification steps. FIG. 5 shows that the smFISH signal for AgRP (left) was effectively removed after a 20 min exposure to RNaseH at 40° C. to degrade DNA/RNA complexes (middle; and step 1 in cartoon schematic above photographs). An additional step involving a 30 min incubation at 65° C. in H2O (step 2 in cartoon) served to inactivate RNase H and remove the branched DNA chain (after degradation of the mRNA/DNA complex), and re-amplification revealed low to undetectable levels of mRNA-related signal, indicating successful stripping (right). This method is referred to herein as "smartFISH".

Example 5—RNase H Stripping Eliminates mRNA Complexed With bDNA Probes

Figure 6:
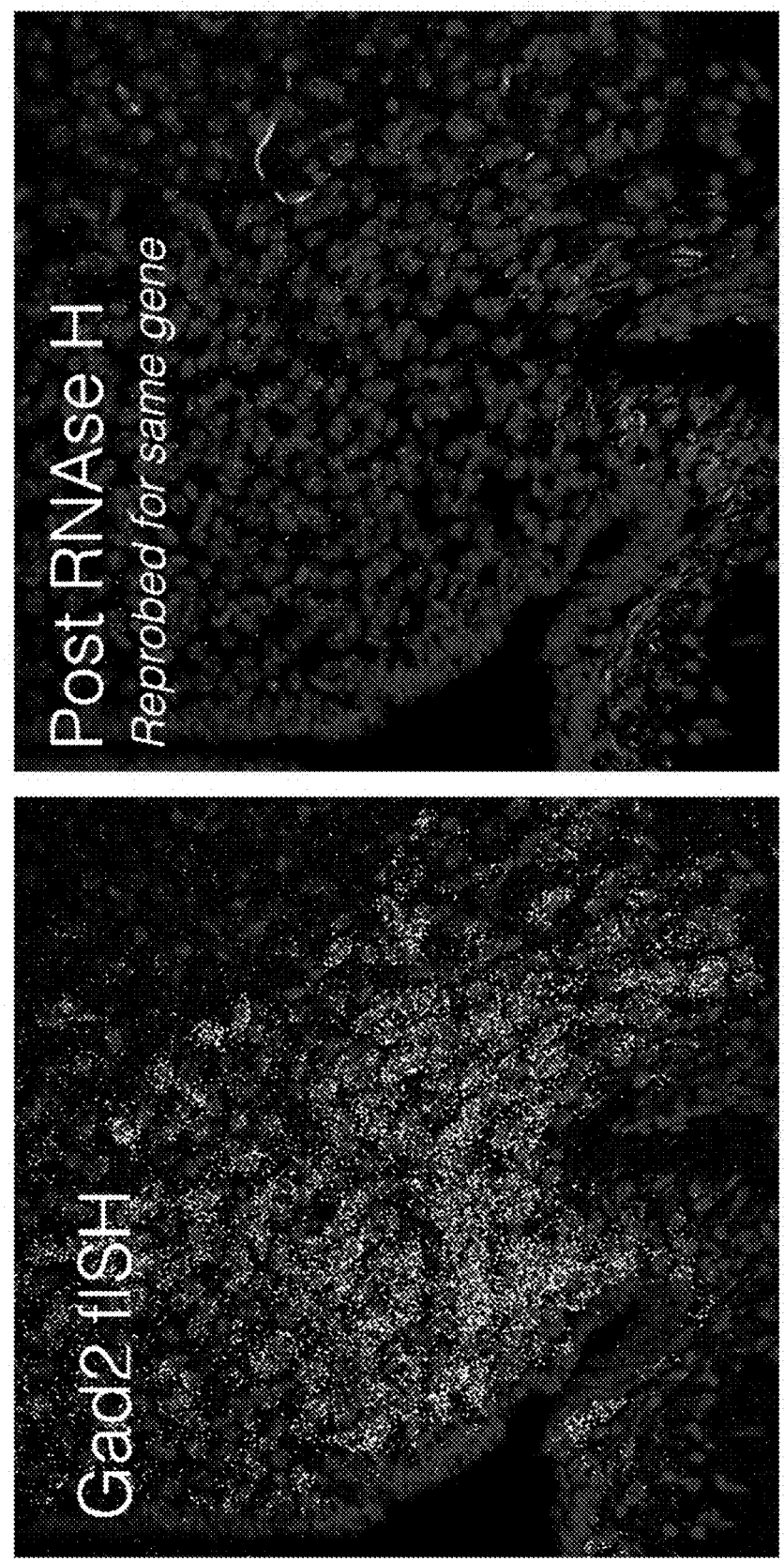
FIG. 6 are photographs showing that RNaseH stripping eliminates mRNA complexed with bDNA probes. Left panel, bDNA FISH amplification and binding with Gad2; Right panel, bDNA FISH amplification and binding with Gad2 following stripping with RNase H.

Importantly, attempts to re-probe tissue in order to label an mRNA species identical to that probed in a previous round produced no signal after enzymatic stripping, which indicates near-total elimination of all mRNA species associated with the gene of interest. FIG. 6 shows that Gad2 mRNA signal, detected via bDNA RNA-smFISH (left, white), was effectively removed after exposure to RNaseH.

Re-probing for the same gene revealed extremely limited signal detected using identical imaging conditions (right, white). These results demonstrated that RNaseH-mediated degradation of smFISH signal occurred via selective and comprehensive degradation of mRNA species that were complexed with DNA probes.

Example 6—Serial Multiplexing Using bDNA smartFISH

Figure 7:
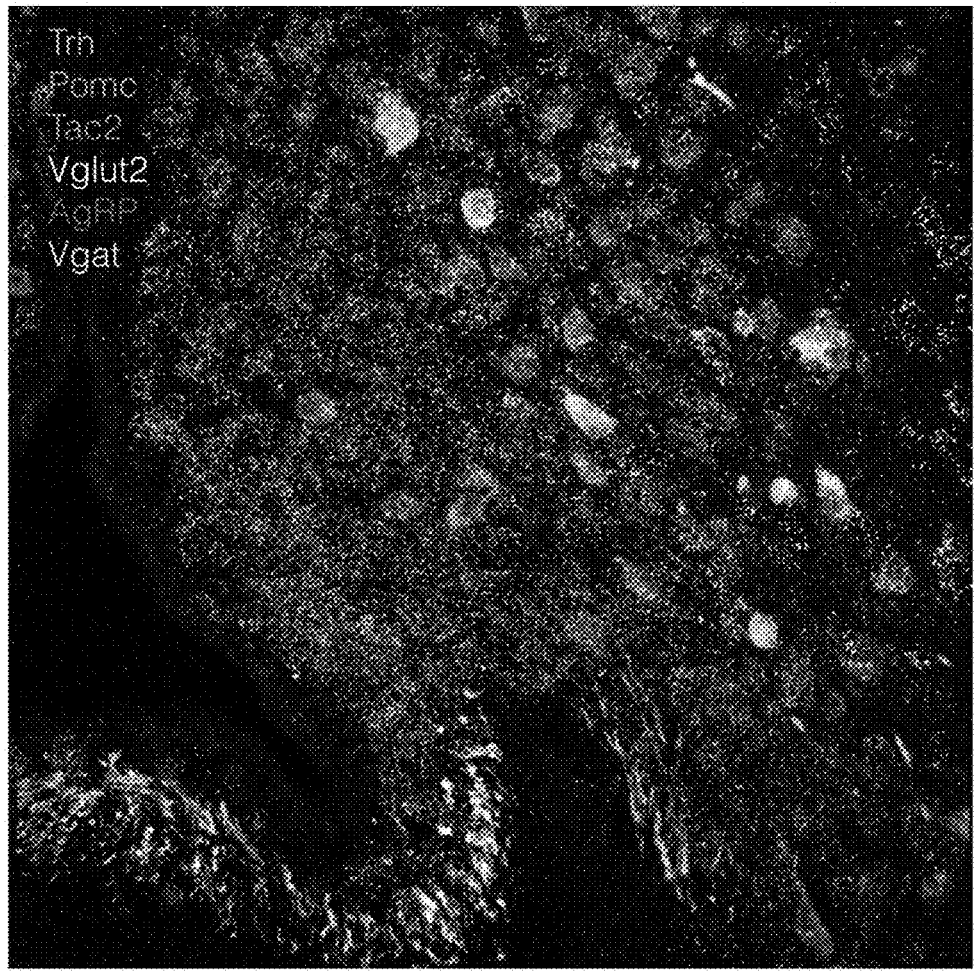
FIG. 7 is a photograph showing serial multiplexing using bDNA smartFISH. Blue, Trh; Green, Pomc; Purple, Tac2; White, Vglut2; Red, AgRP; Yellow, Vgat.

After RNaseH stripping, it was shown that multiple subsequent rounds of three-plex bDNA RNA-smFISH could be performed with high signal-to-noise ratio and excellent tissue integrity. The simultaneous labeling of six genes in the mouse hypothalamus was demonstrated. For ease of viewing, FIG. 7 shows the product of two rounds of three-plex labeling, although three or more rounds were performed with virtually undetectable degradation of tissue integrity.

Example 7—Immunohistochemistry After bDNA smartFISH

Figure 8:
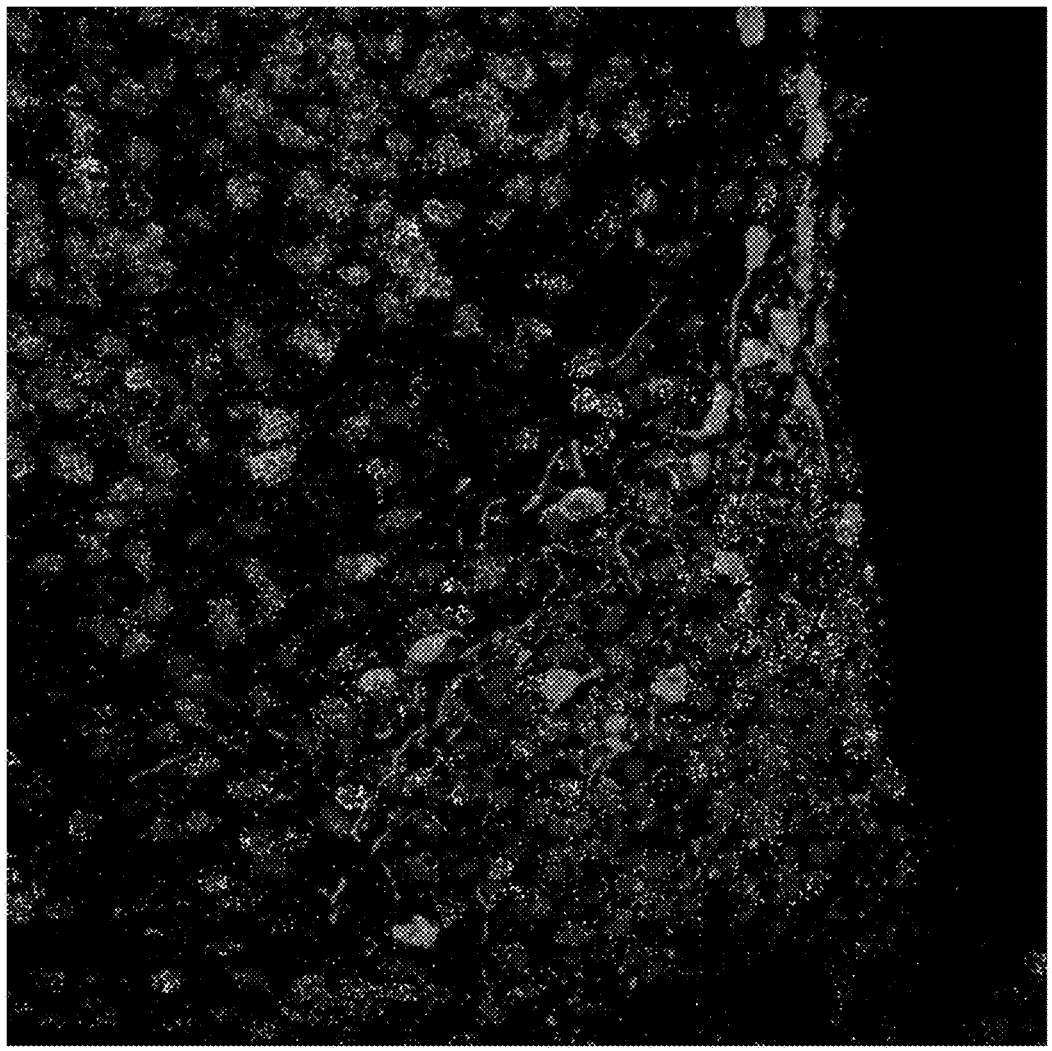
FIG. 8 is a photograph showing tissue integrity with IHC after bDNA smartFISH.

It also was shown that smartFISH was compatible with immunohistochemical detection with antibodies, providing a means to combine molecular profiling with protein quantification on a single cell basis in situ. FIG. 8 shows a region of the mouse hypothalamus in which mRNA associated with the genes vgat (yellow) and vglut2 (green) were detected using bDNA smartFISH. After enzymatic stripping using RNaseH, the tissue was then subject to immunohistochemical detection of the proteins NeuN (blue) and tyrosine hydroxylase (magenta) using standard methods.

Example 8—Effective Removal of bDNA FISH Probes Using DNase

A method to achieve multiplexed labeling of ≥12 genes in situ is described herein (referred to herein as "multiFISH"). This method uses sequential rounds of RNA-FISH with bDNA-probes and uses DNase to strip the probes and amplification oligonucleotides. Unlike the RNase H stripping method described herein, the same gene can be probed in subsequent FISH rounds. In addition, this method avoids the elevated temperatures used in the RNase H stripping method.

Figure 9:
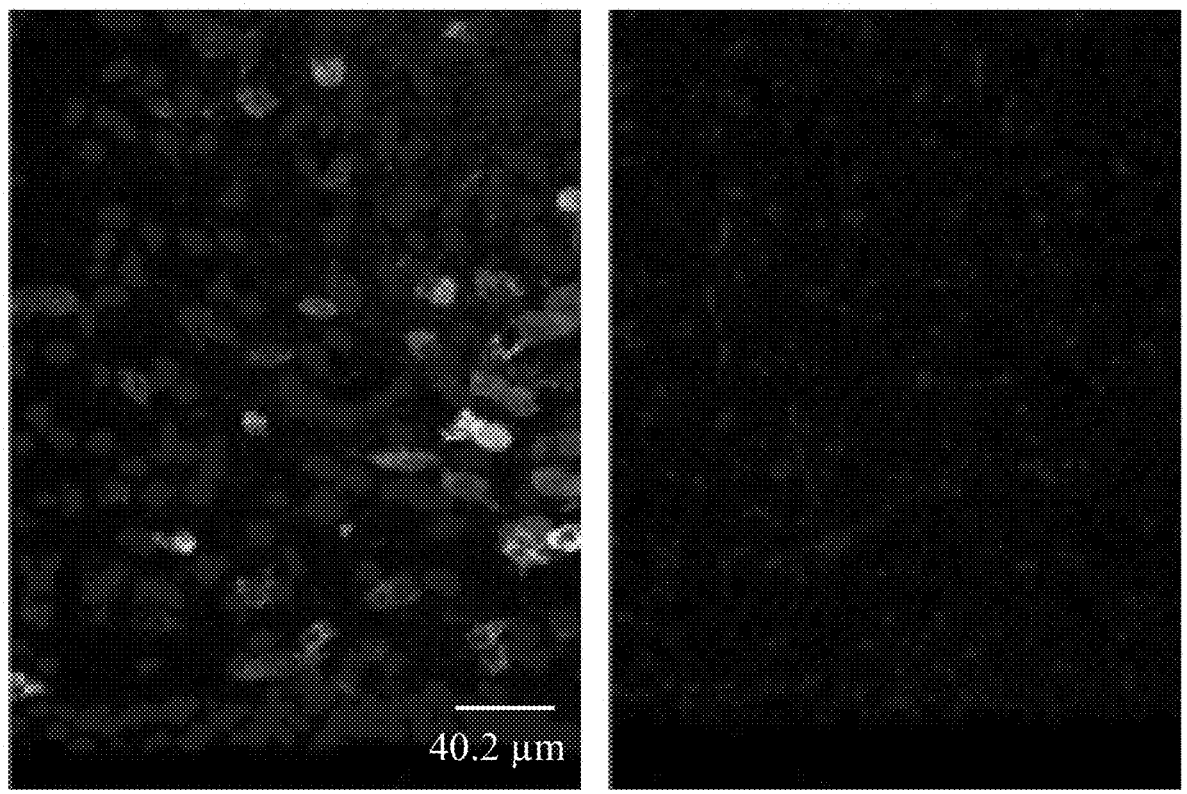
FIG. 9 are photographs showing that DNase I completely removes bDNA probes and amplification oligonucleotides. Left panel, three genes, Avp (green), Sst (red), and Trh (yellow) were detected with 3-plex RNAscope®, a bDNA-based RNA-FISH platform. Cellular nuclei are stained with DAPI (blue). Right panel, after DNase I stripping and subsequent application of amplification oligonucleotides in the absence of gene specific probes, no FISH signals were observed. Also, nuclei are no longer reliably stained with DAPI (imaging settings identical to Right panel).
Figure 10:
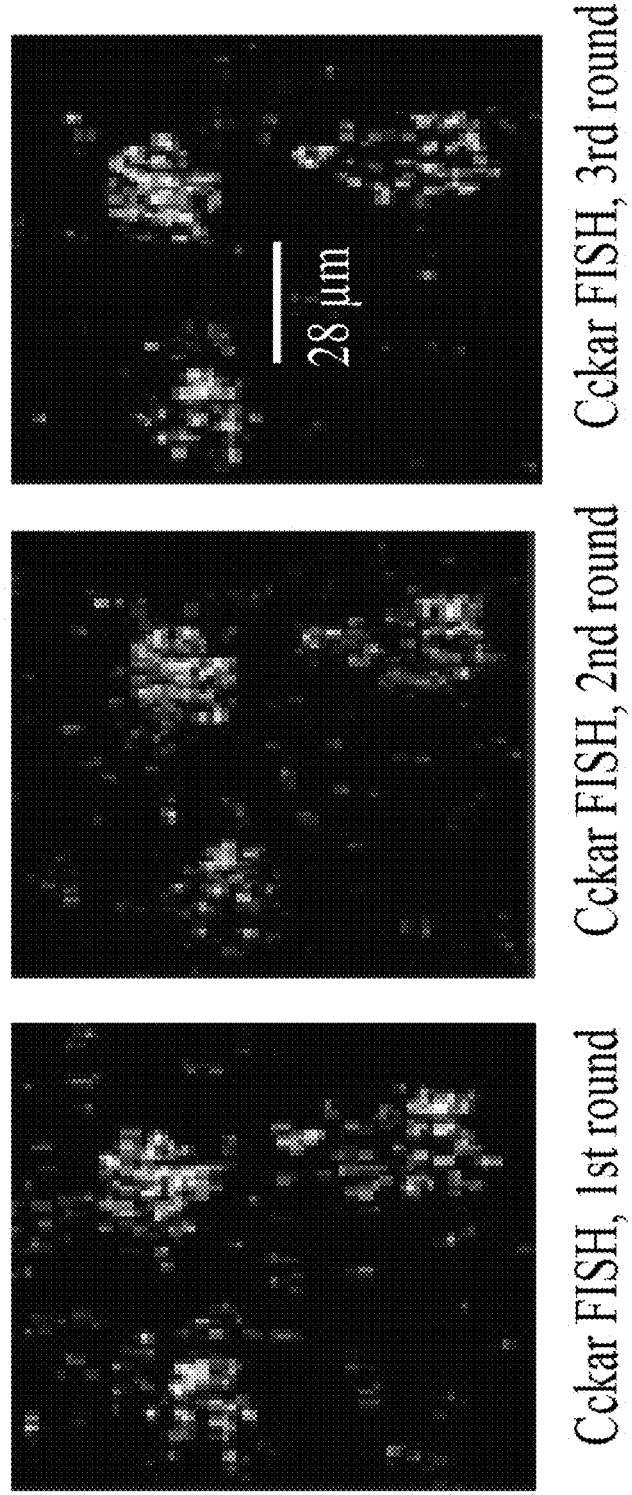
FIG. 10 are photographs showing that the same gene can be stripped and re-probed. The gene Cckar was sequentially probed and DNase1 stripped in 3 rounds of FISH.

An experimental procedure has been developed for multiple rounds of bDNA RNA-FISH on the same tissue sample by stripping bDNA probes and amplification oligonucleotides with DNase I. Recombinant RNase-free DNase I can be inactivated by washing in phosphate buffered saline (PBS). Thus, DNase I can be eliminated by PBS washing after stripping and before the next round of FISH. This method ensures thorough removal of the probes (FIG. 9) and permits subsequent re-probing (FIG. 10).

Example 9—Alignment of Tissue Sections After Multiple Rounds of Probing and Stripping Because DAPI-stained nuclei are typically used to align the same tissue section across multiple rounds of RNA-FISH, one limitation to using DNase to strip FISH probes is that the DNA that binds DAPI is substantially degraded after digesting the first round of bDNA FISH probes, limiting the application of automated alignment algorithms for the same tissue sample across multiple rounds of FISH.

Figure 11:
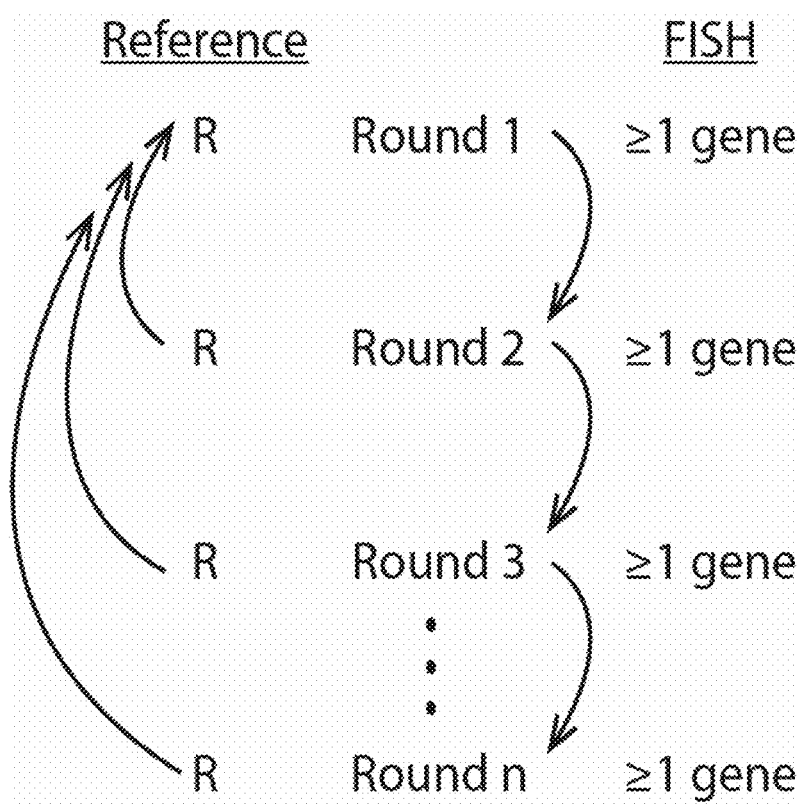
FIG. 11 is a schematic showing that alignment of a tissue sample across multiple rounds of FISH requires a reference (R) tissue marker that can be used to align with cellular resolution. A fluorescent staining pattern in the tissue that has a consistent appearance can be simultaneously imaged and used as the reference with each round of FISH.
Figure 12:
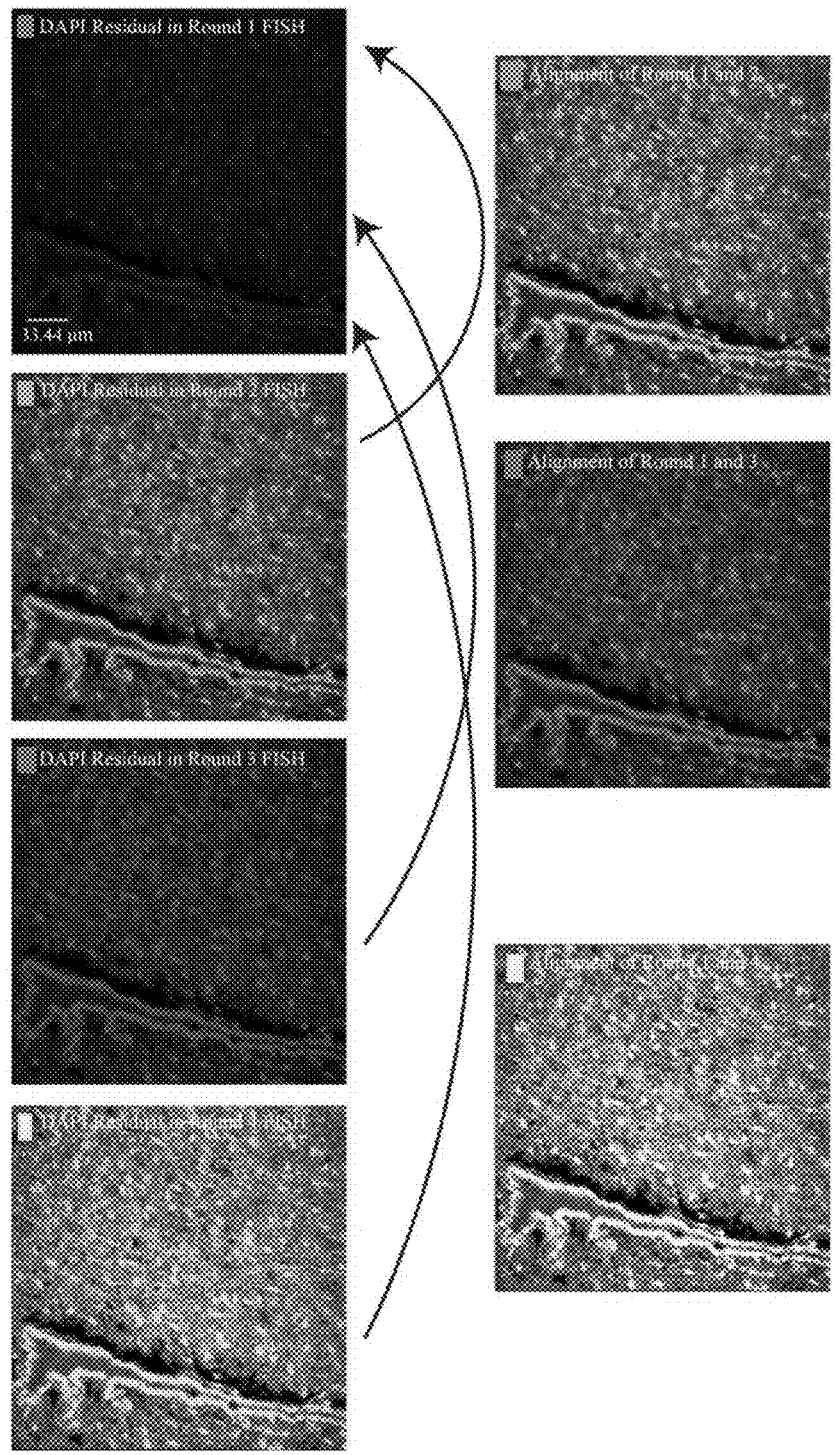
FIG. 12 are images showing the alignment of tissue sections from each round of FISH using DNase I stripping of bDNA probes. Left panels, DAPI staining pattern after DNase I stripping, which is termed DAPI residual. Although nuclear patterns of DAPI staining are not constant across subsequent rounds of FISH, the high frequency fibrous signals remain consistent across at least 4 rounds of FISH. Right panels, with DAPI residual in Round 1 FISH as a reference, each subsequent round of FISH image can be precisely aligned with the residual DAPI signal from Round 1. The high frequency fibrous non-nuclear signal in the images is responsible for successful alignment.
Figure 13:
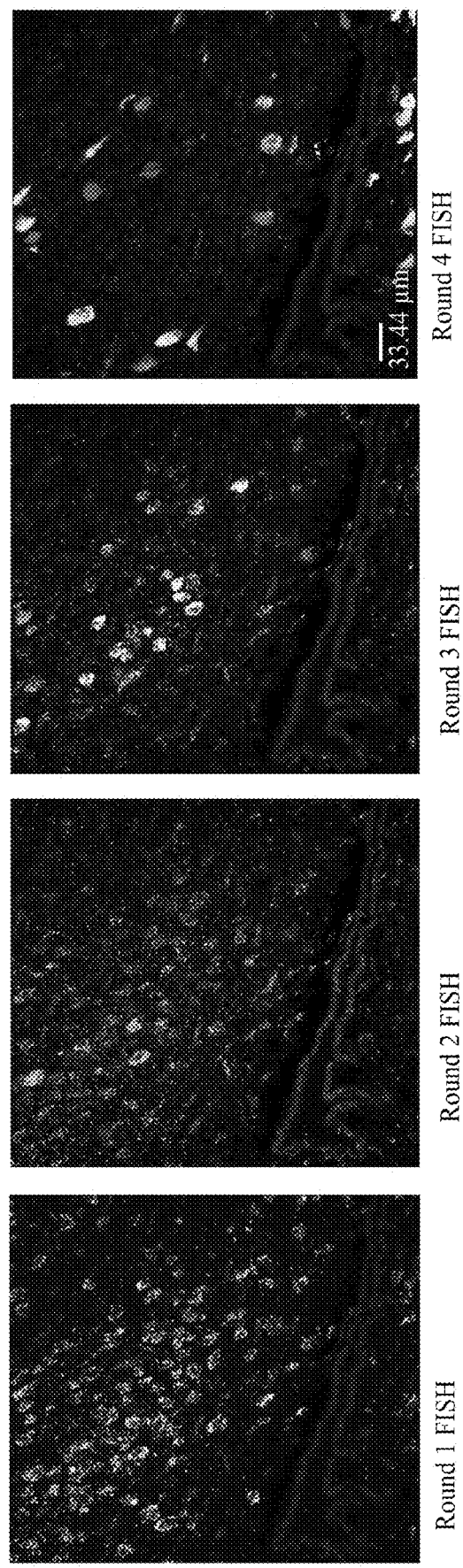
FIG. 13 are photographs showing four rounds of FISH, with 3 distinct transcripts detected in each round, overlaid on their corresponding DAPI staining patterns. Left to right: Vglut2 (green), Gad2 (red), and Syp (yellow) were probed in Round 1; Crh (green), Reln (red), Ntngl (yellow) were probed in Round 2; Pdyn (green), Penk (red), Trh (yellow) were probed in Round 3; and Oxy (green), Avp (red), and Sst (yellow) were probed in Round 4.

Multiple rounds of FISH on the same tissue requires alignment of a reference tissue features across each round (FIG. 11). For this, it was found that, after DNase treatment, DAPI stains a combination of nuclear and high frequency fibrous non-nuclear features that are stable across multiple rounds of FISH (FIG. 12). Using these stable DAPI-binding features, non-linear registration algorithms can be used to align three dimensional images of these tissue sections with high precision by combining three-dimensional affine transformation and non-linear deformation transformation using, for example the Advanced Normalization Tools software package (FIG. 12). This algorithm achieves automated computational alignment of tissue section across multiple rounds of FISH images over at least four rounds of 3-plex FISH for a total of 12 FISH probes aligned with cellular resolution on a single tissue sample (FIG. 13).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:
1. A method for producing a second branched probe set-bound cell or tissue, comprising:
   contacting a cell or a tissue with a first branched DNA probe set under fluorescent in situ hybridization (FISH) conditions in which the first branched DNA probe set is taken up into the cell or the cells of the tissue, wherein the first DNA branched probe set binds to a first set of RNAs in the cell or the cells of the tissue, thereby producing a first branched probe set-bound cell or tissue;
   obtaining an image of the first branched DNA probe set-bound cell or tissue;
   contacting the first branched probe set-bound cell or tissue with RNase H to remove the first branched probe set from the first set of RNAs in the cell or the tissue;
   performing a first wash step by washing the cell or the tissue, thereby removing the first branched probe set and the RNase H from the cell or the tissue; and
   after the first washing step, contacting the cell or the tissue with a second branched DNA probe set under fluorescent in situ hybridization (FISH) conditions in which the second branched probe set is taken up into the cell or the cells of the tissue, wherein the second DNA probe set binds to a second set of RNAs in the cell or the cells of the tissue and each of the first branched DNA probe set and the second branched DNA probe set is labeled with a fluorescent dye, thereby producing the second branched probe set-bound cell or tissue.

2. The method of claim 1, further comprising: contacting the second branched DNA probe set-bound cell or tissue with RNase H to remove the second branched DNA probe set from the second set of RNAs in the cell or the tissue; performing a second wash step by washing the cell or the tissue, thereby removing the second branched DNA probe set and the RNase H from the cell or the tissue; and after the second wash step, contacting the cell or the tissue with a third branched DNA probe set under fluorescent in situ hybridization (FISH) conditions in which the third branched DNA probe set is taken up into the cell or the cells of the tissue, wherein the third branched DNA probe set binds to a third set of RNAs in the cell or the cells of the tissue and the third branched DNA probe set is labeled with a fluorescent dye, thereby producing a third branched DNA probe set-bound cell or tissue.

3. The method of claim 2, further comprising: contacting the third branched DNA probe set-bound cell or tissue with RNase H to remove the third branched DNA probe set from the third set of RNAs; performing a third wash step by washing the cell or the tissue, thereby removing the third branched DNA probe set and the RNase H from the cell or the tissue; and after the third wash step, contacting the cell or the tissue with a fourth branched DNA probe set under fluorescent in situ hybridization (FISH) conditions in which the fourth branched DNA probe set is taken up into the cell or the cells of the tissue, wherein the fourth branched DNA probe set binds to a fourth set of RNAs in the cell or the cells of the tissue and the fourth branched DNA probe set is labeled with a fluorescent dye, thereby producing a fourth branched DNA probe set-bound cell or tissue.

4. The method of claim 3, further comprising: contacting the fourth branched DNA probe set-bound cell or tissue with RNase H to remove the fourth branched DNA probe set from the fourth set of RNAs; performing a fourth wash step by washing the cell or the tissue, thereby removing the fourth branched DNA probe set and the RNase H from the cell or the tissue; and after the fourth wash step, contacting the cell or the tissue with a fifth branched DNA probe set under fluorescent in situ hybridization (FISH) conditions in which the fifth branched DNA probe set is taken up by the cell or the cells of the tissue, wherein the fifth branched DNA probe set binds to a fifth set of RNAs in the cell or the cells of the tissue and the fifth branched DNA probe set is labeled with a fluorescent dye, thereby producing a fifth branched DNA probe set-bound cell or tissue.

5. The method of claim 2, further comprising:
obtaining an image of the second branched DNA probe set-bound cell or tissue.

6. The method of claim 5, further comprising aligning the image of the second branched DNA probe set-bound cell or tissue with the image of the first branched DNA probe set-bound cell or tissue.

7. The method of claim 1, wherein the first branched DNA probe set and/or the second branched DNA probe set comprise/comprises more than one branched DNA oligonucleotide probe.

8. The method of claim 1, wherein the first branched DNA probe set and/or the second branched DNA probe set comprise/comprises a plurality of branched DNA oligonucleotide probes.

9. The method of claim 1, wherein each branched DNA oligonucleotide probe in the first branched DNA probe set and the second branched DNA probe set comprises a differentially fluorescent label.

\* \* \* \* \*